(12) United States Patent
Eswara

(10) Patent No.: US 10,583,059 B2
(45) Date of Patent: Mar. 10, 2020

(54) NEONATE INCUBATOR SYSTEM AND METHOD

(71) Applicant: General Electric Company, Schenectady, NY (US)

(72) Inventor: Ganesh Prasad Eswara, Bangalore (IN)

(73) Assignee: General Electric Company, Schenectady, NY (US)

( * ) Notice: Subject to any disclaimer, the term of this patent is extended or adjusted under 35 U.S.C. 154(b) by 374 days.

(21) Appl. No.: 15/458,175

(22) Filed: Mar. 14, 2017

(65) Prior Publication Data

US 2018/0263835 A1    Sep. 20, 2018

(51) Int. Cl.
*A61G 11/00*    (2006.01)
*A61M 16/16*    (2006.01)
*A61M 16/00*    (2006.01)
*A61G 10/02*    (2006.01)

(52) U.S. Cl.
CPC .............. *A61G 11/00* (2013.01); *A61G 10/02* (2013.01); *A61M 16/0051* (2013.01); *A61M 16/16* (2013.01); *A61M 2205/18* (2013.01); *A61M 2205/3327* (2013.01)

(58) Field of Classification Search
CPC ... A61G 10/02; A61G 11/00; A61M 16/0051; A61M 16/16; A61M 2205/18; A61M 2205/3327; A61M 2205/3389
See application file for complete search history.

(56) References Cited

U.S. PATENT DOCUMENTS

2015/0182722 A1    7/2015  Lesch et al.

*Primary Examiner* — Christine H Matthews
(74) *Attorney, Agent, or Firm* — Andrus Intellectual Property Law, LLP

(57) ABSTRACT

An incubator system for a neonate includes a humidifier containing a water reservoir and a water age module that detects a cleaning event of the water reservoir, determines a water age based on a duration since the cleaning event, and compares the water age to a preset expiration time. Once the water age exceeds the present expiration time an expiration alert is generated.

20 Claims, 6 Drawing Sheets

NEONATE INCUBATOR SYSTEM AND METHOD

BACKGROUND

Neonatal incubators create a micro environment that is thermally neutral where a neonate can develop. These incubators typically include a humidifier and associated control system that controls the humidity in the neonatal microenvironment. The humidifier comprises a device that evaporates an evaporant, such as distilled water, to increase relative humidity of air within the neonatal microenvironment. Such humidifiers typically have an evaporant source in the form of a reservoir that holds evaporant to be dispersed into the microenvironment within the incubator. For example, the humidifier may be an evaporative humidifier in which air is passed through a screen, wick, or other evaporate carrier to pick up moisture. In another embodiment, the humidifier may be a steam humidifier or vaporizer in which water is heated to cause evaporation. In yet another implementation, the humidifier comprises an impeller in which a rotating disk propels water at a cone-like diffuser to break the water into tiny droplets that float in the air. The humidifier is adjustable and controllable such that the rate at which water or water vapor is added to the microenvironment may be adjusted in order to control the humidity to a desired value.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment an incubator system for a neonate includes a humidifier containing a water reservoir and a water age module that detects a cleaning event of the water reservoir, determines a water age based on a duration since the cleaning event, and compares the water age to a preset expiration time. Once the water age exceeds the present expiration time, the water age module generates an expiration alert.

One embodiment of a method of controlling an incubator system for a neonate, the incubator system having a humidifier that disperses water from a water reservoir, includes generating a water level indicator value based on a water level in a water reservoir of a humidifier, and detecting a cleaning event of the water reservoir based on the water level indicator value. A date and time of the cleaning event are determined, and a preset expiration time is then determined based on the date and time of the cleaning event. An expiration alert is then generated once a water age exceeds the preset expiration time.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Through extensive experimentation and research in the field of neonatal incubators, the present inventor has recognized that a problem exists where reservoirs of humidifiers are not drained and cleaned frequently enough, which introduces a risk of infection to the baby occupying an incubator. For example, the inventor has recognized that humidifier reservoirs may not be emptied and cleaned frequently enough or between each patient, and occasionally caregivers reuse water existing in the reservoir and simply add additionally fresh water when a new baby is placed in an incubator. This practice has the potential of contamination and spreading infection to the new baby. Additionally, contamination may develop in a water reservoir over time, even over the course of housing a single occupant infant. In view of the forgoing, the inventor recognized that a tracking system is needed to track whether a water reservoir of a humidifier is in need of cleaning, such as to detect reservoir cleaning and track the amount of time that has passed since the reservoir has been cleaned.

Figure 1:
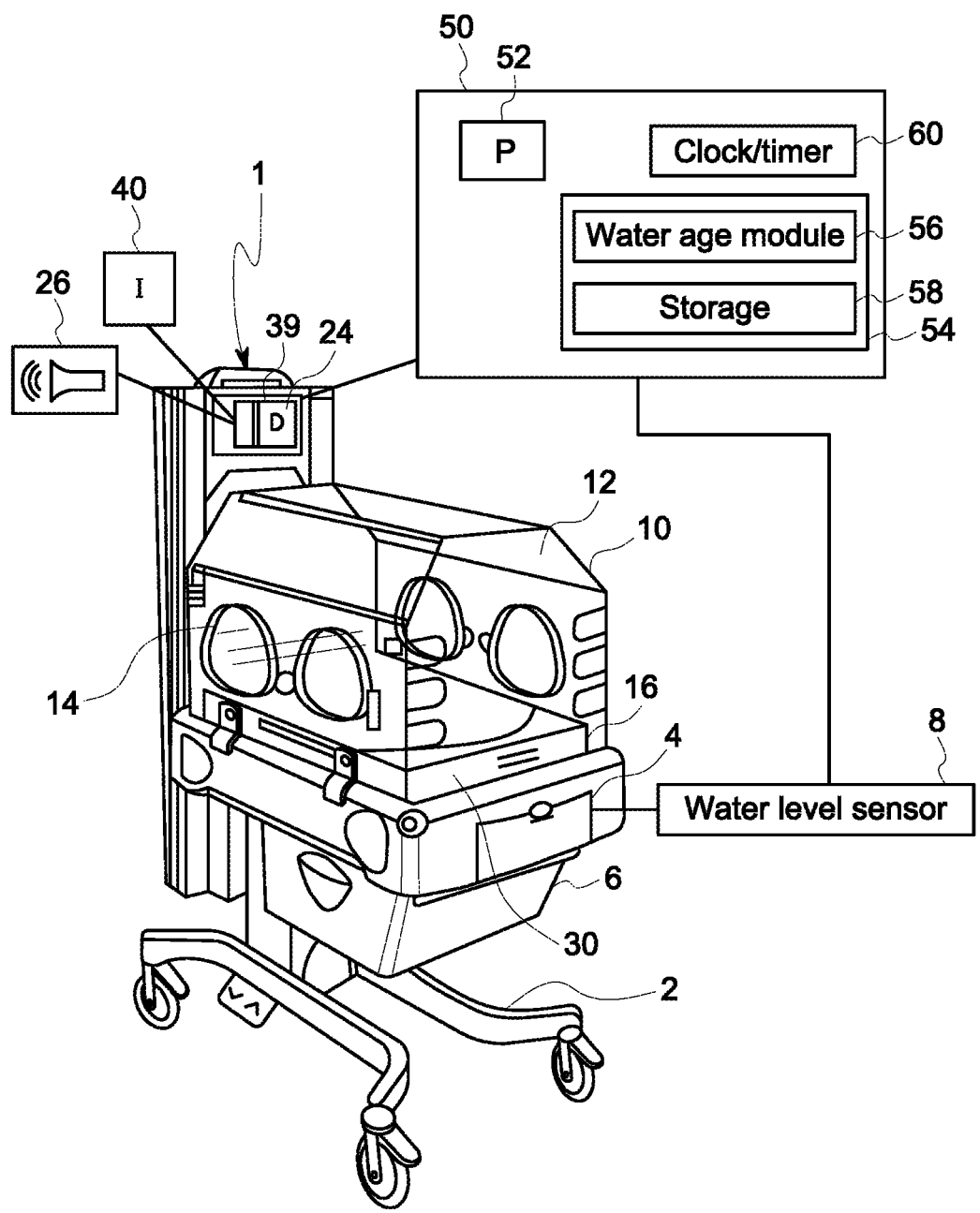
FIG. 1 is a perspective view of an example incubator containing a humidifier, also including a schematic diagram depicting relevant sensing and control elements of the incubator system.

FIG. 1 depicts one embodiment of an incubator system 1 having a bed 16 supported by a base 2. In the depicted embodiment, the base 2 is on wheels to facilitate transit of an infant in the incubator system 1. The depicted incubator system 1 has a hood 10 defining a chamber 12 creating a microenvironment for housing a neonate. The hood 10 comprises a transparent housing extending about the bed 16. In the example illustrated, the hood 10 includes a plurality of portholes 14 through which a healthcare provided may access the one or more infants within the chamber 12. In the illustrated example, the hood 109 comprises a single structure moveable as a unit. In other implementations, sidewalls of the hoods 10 may remain about the bed 16 forming a crib, wherein the top-most portion is separable from the sidewalls to access the one or more infants.

The bed 16 may further include heating component(s) 30 used to control the temperature within the microenvironment of the chamber 12. For example, the heater 30 may be a radiant heating or warming device that heats the air within the chamber 12 to a predefined temperature or within a predefined temperature range. In another embodiment, the heater 30 may comprise a convective or conductive heating device or any other type of heating or warming device.

The incubator system 1 further includes a humidifier 4 controllable to adjust the relative humidity within the chamber 12. The humidifier comprises a device that evaporates an evaporant, such as distilled water 7, to increase relative humidity of air within the neonatal microenvironment. The humidifier 4 has a water reservoir 6 containing evaporant, such as distilled water, utilized for humidification of the chamber 12. The water reservoir 6 is a tank or other vessel capable of holding the evaporant. Although the water reservoir 6 in the illustrated embodiment is located below the bed 16, in other embodiments the water reservoir 6 may be provided at other locations. In one embodiment, the water reservoir 6 is removable from the incubator system 1 for draining and/or cleaning purposes. In other embodiments, the reservoir 6 may remain attached to the incubator system 1 and may provide other access for the purpose of draining the evaporant from the reservoir 6 and/or cleaning the reservoir 6. A water level sensor 8 senses the water level 33 within the reservoir 6 and generates a water level indicator value, as described in more detail below.

The incubator system 1 also comprises a control system 50 that controls various elements on the incubator system 1, including the humidifier 4. The control system 50 may be housed on the incubator, or may be or include an external control system portion (e.g. that communicates wirelessly with various other aspects of the system. In the depicted embodiment, the control system 50 includes a processing system 52 and a memory 54. The processing system 52 comprises one or more processors configured to carryout instructions or code contained in memory 54. The processing system 52 may be part of, or may include, an application specific integrated circuit (ASIC) an electronic circuit, a combinational logic circuit, a field programmable gate array (FPGA), a processor (shared, dedicated, or group), and/or other suitable components that provide the functionality described herein. The term code, as used herein, may include software, firmware, and/or microcode, and may refer to programs, routines, functions, classes, and/or objects. Memory 54 comprises storage 58 for storing data, such as data comprising part of a cleaning log as described herein.

The memory further includes a water age module 56, which is a set of software instructions, or code, executed to carry out the methods and controls described herein. The control system 50 further includes a clock or timer 60 utilized to calculate water age, i.e. a water age timer, as described herein. Non-limiting examples of memory 54 includes non-volatile memory, magnetic storage, and optical storage. The water age module 56 monitors the age of the water in the reservoir 6 and provides an alert to a clinician via the user interface 39 when the water age has exceeded a preset expiration time. In certain embodiments, the water age module 56 may also monitor a water level 33 of water 7 in the water reservoir 6, or it may receive a water level 33 value from another module or device charged with monitoring the amount of water 7 in the water reservoir 6. Additionally, the water age module 56 may instruct or facilitate controlling the humidifier to stop operation until the reservoir 6 has been cleaned.

In the depicted embodiment, the incubator system 1 further includes a user interface 39 comprising a display 24, a speaker 26, and an input 40. Such user interface 39 elements are used to provide information to a clinician regarding the status and condition of the incubator system 1, as well as to receive control inputs from a clinician to control various aspects of the incubator system 1, including to control the environment within the chamber 12. The display 24 includes any visual output device, examples of which include a digital display screen, monitor, or the like (which may also be a touchscreen) that presents visible notifications or messages to a clinician. The display 24 may include a monitor independent of the bed-portion of the incubator incorporated into some portion. In another implementation, the display 24 may comprise a screen of a portable computing or electronic device, such as a smartphone or tablet computer. Likewise, the speaker 26 may be any audio output device and may be incorporated into the bed portion of the incubator system, or may be included in a separate device, such as in the personal computing device described above. Likewise, the input 40 may be any device that facilitates user input of information, such as commands, selection, data, or settings for the incubator system 1. In one implementation, the input 40 may include a keyboard, touchpad, touchscreen, mouse, or microphone with speech recognition software, or the like.

Figure 2:
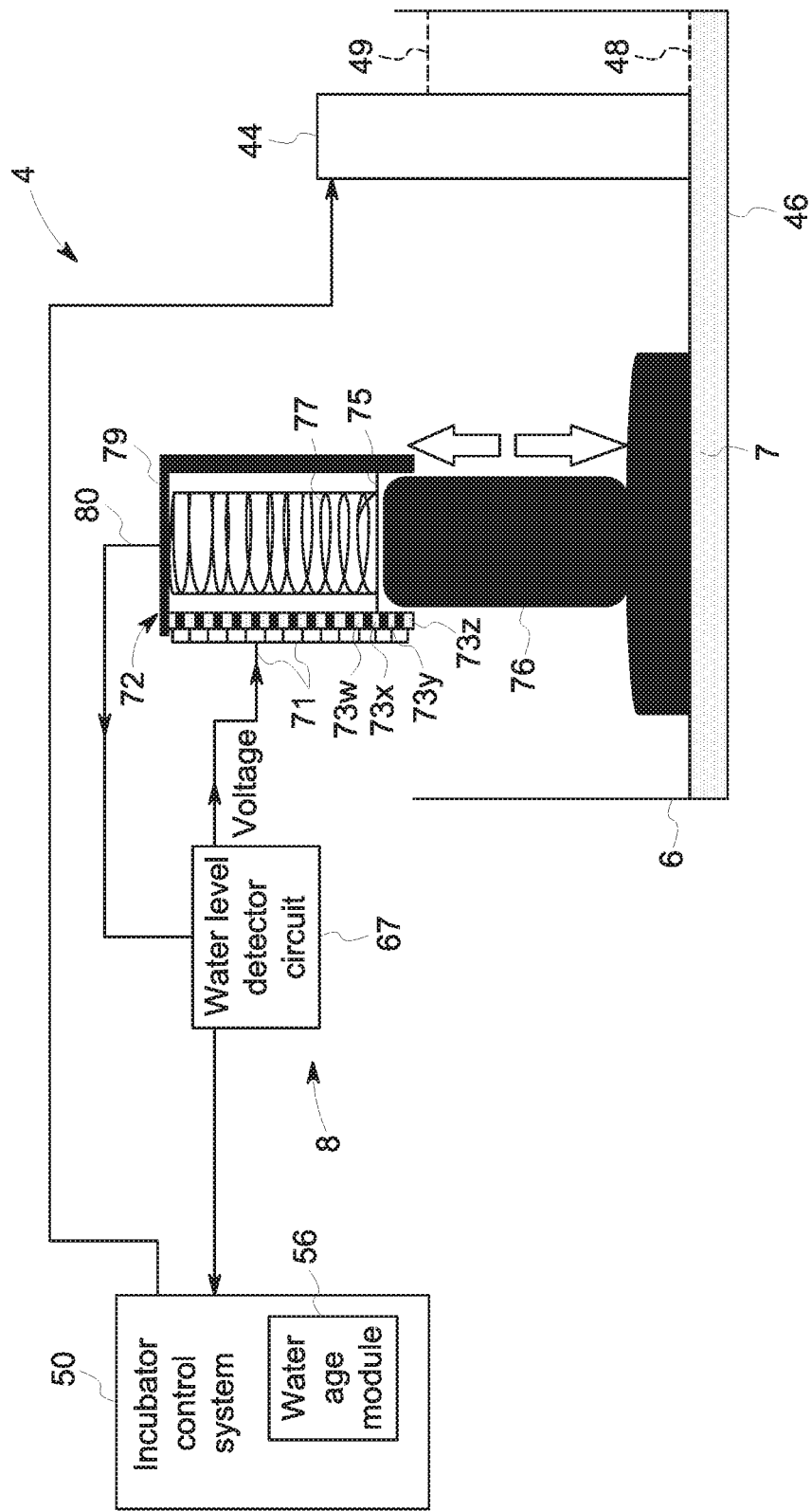
FIG. 2 is a schematic diagram of a water reservoir and water level sensor connected to an incubator control system.

FIG. 2 depicts one embodiment of a water level sensor 8 that measures a water level 33 at or with respect to a base 46 of the water reservoir 6. The Figure depicts just one example of a system sensing a water level 33 in the reservoir 6 and generating a water level indicator value. The inventor recognizes that other water level sensors 8 having other water level detection circuits or devices are possible, and contemplates that any device or system capable of sensing the water level and communicating a water level indicator value to the control system 50 may be utilized.

In the exemplary embodiment of FIG. 2, the water level sensor 8 comprises a water level detector circuit 67 that supplies a voltage, via conductors 71, to multiple points on a band of resistors 72, and specifically to each resistor (e.g. 73w-73z) on the band. The band of resistors 72 contains multiple different resistors 73w-73z, each electrically isolated from one another and each having a different resistance value than the others. A moving plate 75 moves up and down along the band of resistors 72 depending on the amount of water 7 held in the reservoir 6. In the depicted embodiment, a buoy 76 floats on top of the water 7 and presses on the moving plate 75. A spring 77 exerts a minimal downward force on the moving plate 75 that is sufficient to maintain the moving plate 75 on top of the buoy 76. The spring 77 is comprised of a conductive material, such as metal, so that it transmits a current between the moving plate 75 and a top plate 79. A conductor 80 connects between the top plate 79 and the water level detector circuit 67. The resistance, and thus the voltage drop, across the water level detector circuit 67 is known, such which is primarily only variable between the conductors 71 and the moving plate 75. Accordingly, the value of the resistor 73w-73z from the band of resistors 72 touching the moving plate 75 can be isolated and determined.

The value of the resistor 73w-73z is then used to determine the level of the water 7 in the reservoir 6 and generate the water level indicator value. In other words, as the water 7 is depleted and the buoy 76 moves down, the moving plate 75 will move down the band of resistors 72. Likewise, as water 7 is added to the water reservoir 6 and the water level 33 goes up, the moving plate 75 will move up the band of resistors 72.

The water level detector circuit 67 outputs a water level indicator value to the control system 50, which contains the water age module 56. The water level indicator value may be any value associable by the water age module 56 with a water level 33. The water level indicator value may be an analogue or digital value. In certain embodiments, the water level detector circuit includes an analogue-to-digital converter or is otherwise capable of generating a digital water level indicator value. To provide just a few examples, the water level indicator value may be the value of the resistor 73w-73z, a resistor location on the band of resistors 72, a voltage drop across the measurement unit, or any other value that is associated with a water level. The water age module 56 may track the water level indicator value over time, such as storing the values in storage 58 to generate a cleaning log that tracks the water level within the reservoir 6 over time.

During normal operation, the control system 50 may generally maintain the water level in the reservoir 6 between a minimum water level 48 and a maximum water level 49. In the depicted example, the minimum water level 48 corresponds to the bottom portion of the evaporation element 44 which facilitate the humidification provided by the humidifier 4. As described above, the evaporation element 44 may be a screen, a wick, a heating element, or any other device that facilitates utilizing the water 7 in the reservoir 6 to humidify the chamber 12 of the incubator system 1. Accordingly, the control system 50 generally instructs maintenance of the water level to maintain the ability of the evaporator 44 to perform its function, and such control function may be incorporated into the water age module 56 or it may be provided by a separate module. In the depicted embodiment, the evaporator 44 needs to maintain contact with the water 7, and thus the control system 50 automatically maintains or provides instruction to a user to maintain the water level above the minimum water level 48. In certain embodiments, the control system 50 may stop operation of the humidifier 4 when the water level falls below the minimum water level 48. A maximum water level 49 is dictated by the size of the reservoir 6, and in other embodiments may also account for other constraints on the system.

Accordingly, some minimum amount of water will typically be maintained in the reservoir 6, at the base 46 thereof, even when new sterile water is added. Thus, contamination that enters the reservoir 6 at any point will continue to exist within the reservoir until the reservoir is emptied and cleaned. Accordingly, the inventor has developed the present system and control method which monitors cleaning of the reservoir 6 and generates an alert when cleaning is needed. Additionally, the system may stop operation of the humidifier 4 when cleaning is needed, so as to thwart the exposer risk caused by the use of expired water within the reservoir 6 and to mandate the cleaning.

In order to verify that the cleaning event has actually occurred, the system 1 may be configured to require that the water level indicator value detected by the water level sensor 8 indicate that all water 7 has been drained from the reservoir 6 and that no water 7 remains at the base 46 of the reservoir. For example, the water age module 56 may be configured to detect a cleaning event based on the water level indicator value if the output of the water level detector circuit 67 indicates that the buoy 76 is touching the base 46 of the reservoir 6, i.e., indicating that there is no water 7 at the base of the reservoir 6. In certain embodiments, this condition can only be achieved if a user has emptied, or drained, all water 7 from the reservoir 6 because the control system 50 will shut off the humidifier 4 when the water level 33 falls below the minimum water level 48. Thus, when the water level indicator value indicates that there is no water 7 at the base 46 of the reservoir 6 that can be associated with a user actively draining the reservoir 6 for the purposes of cleaning.

In other embodiments, a cleaning event may be detected by other means. For example, where the incubator humidifier 4 contains a removable reservoir 6, a cleaning event may be detected where the reservoir 6 is removed from the incubator system 1 and then replaced back onto the incubator system 1. For example, the incubator system 1 may have a switch or contact sensor that senses removal and replacement of the reservoir 6. In still other embodiment, the system may detect a cleaning event based on alternative or additional parameters.

Figure 3:
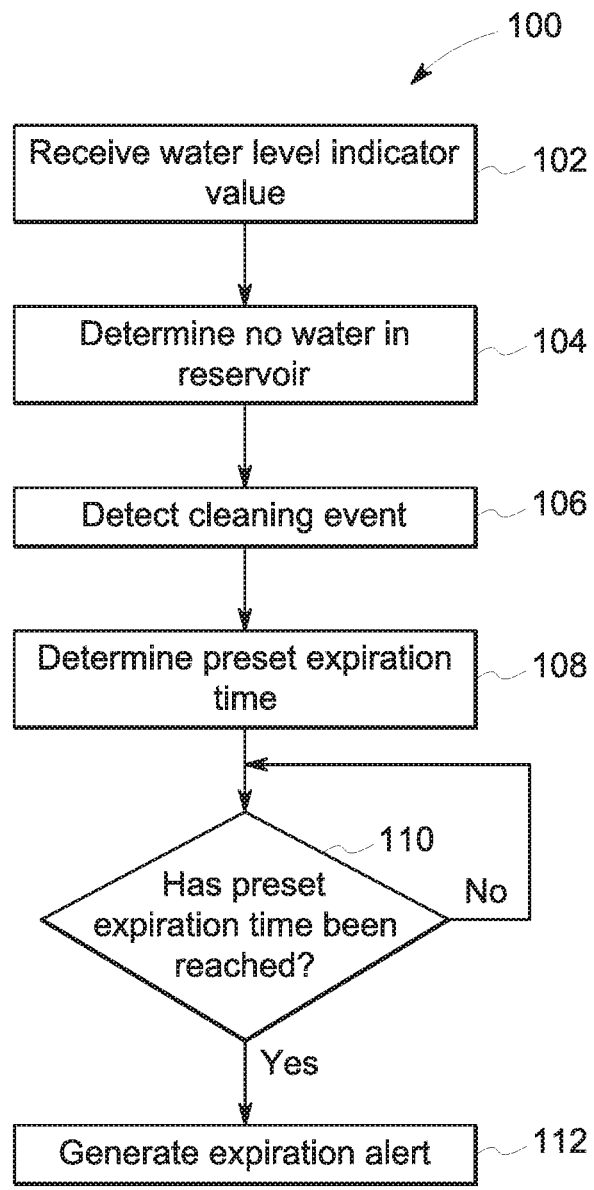
FIG. 3 depicts one embodiment of a method of controlling an incubator system.

FIG. 3 depicts one embodiment of a method 100 of controlling an incubator system 1 having a humidifier 4. In one example, the water age module 56 comprises computer executable instructions, or code, that instruct execution of the steps and logic described herein. In the method 100 represented at FIG. 3, a water level indicator value is received at step 102 and a determination is made at step 104 based on the water level indicator value that there is no water in the reservoir 6. A cleaning event is then detected at step 106. Step 108 is executed to determine a preset expiration time that represents when the reservoir 6 will need to be cleaned again. The present expiration time may be determined and monitored, such as a period of time following the cleaning event or a predetermined date and time calculated based on the date and time of the cleaning event. Step 110 is executed to determine whether the preset expiration time has been reached, such as whether the preset amount of time has passed or the preset date and time has been reached. Once that condition is met, an expiration alert is generated at step 112 to alert a clinician to the need for cleaning the reservoir 6. For example, the alert may include an auditory alarm generated by the speaker 26 and/or a visual alert or instruction displayed on the display 24.

Figure 4:
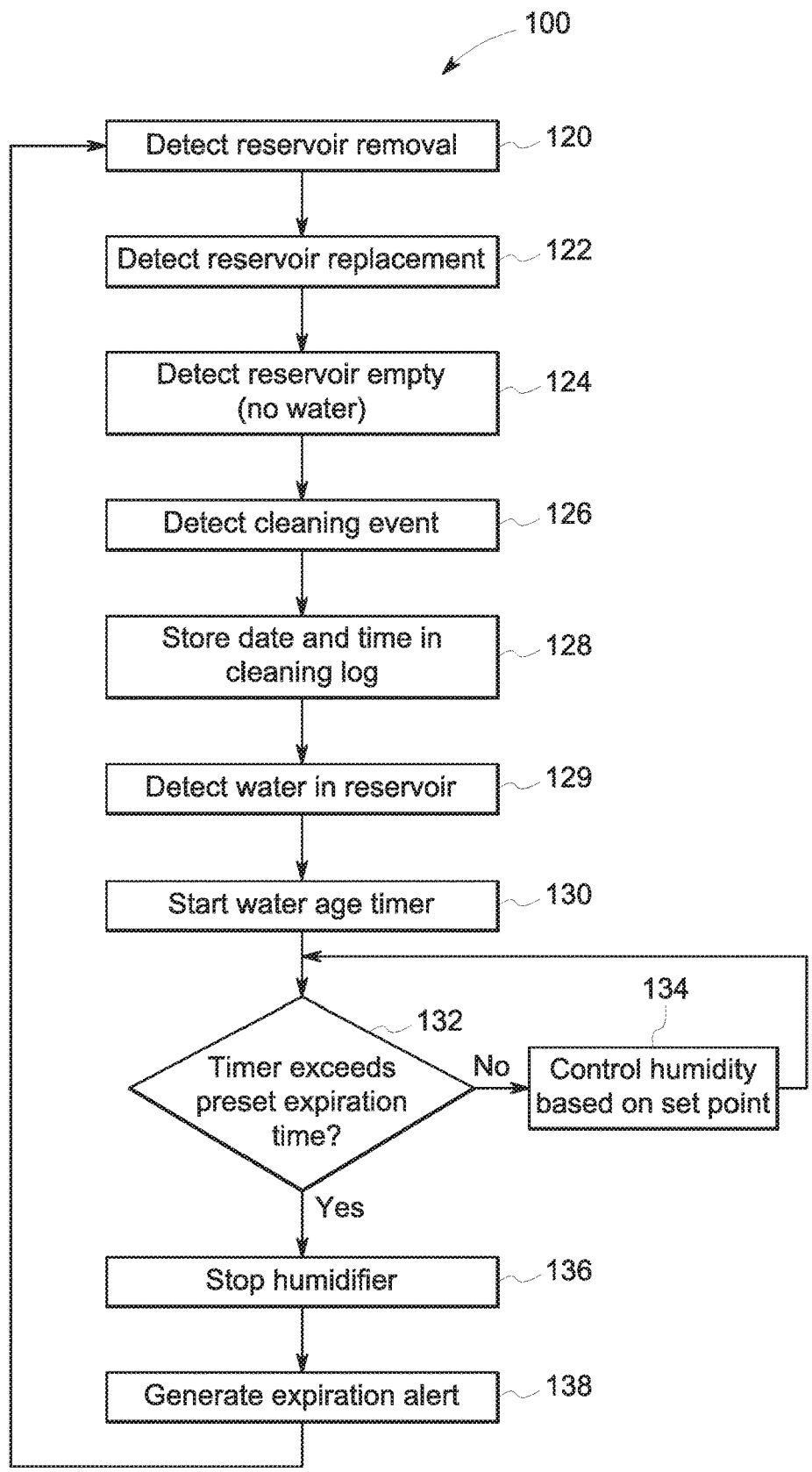
FIG. 4 depicts another embodiment of a method of controlling an incubator system.

FIG. 4 is a flow chart depicting another embodiment of a method 100 of controlling an incubator system 1. In the depicted embodiment, removal of the reservoir 6 is detected at step 120 and replacement of the reservoir 6 is detected at step 122. At step 124 logic is executed to determine that the reservoir does not contain any water. For example, such determination may be made based on the water level indicator value as described above. In other embodiments the absence of water in the reservoir may be detected by other means, such as based on the weight of the reservoir 6 or sensors within the reservoir 6. A cleaning event is then detected at step 126 based on the fact that the reservoir 6 has been removed and replaced in an empty state (containing no water). Thus, cleaning of the reservoir 6 and/or replacement with a clean reservoir 6 is assumed, and the date and time of the replacement is stored at step 128 as a cleaning event date and time. Water is then detected in the reservoir 6 at step 129, such as based on the water level indicator value. In another embodiment, the system may be configured to require an input from a clinician, such as via the input system 40, to indicate that water has been placed into the reservoir 6. A timer is then started at step 130 starting at the date and time of the water input. The timer is then monitored at step 132, and the humidity is controlled by the incubator control system 50 at step 134 using the humidifier 4 according to the standard operation of the incubator system 1, such as based on a humidity setpoint for the microenvironment. Once the timer exceeds the preset expiration time, the humidifier is stopped at step 136 such that it does not disperse any more water 7 from the reservoir 6. Thus, the humidifier 4 cannot be operated to disperse water from the reservoir 6 into the microenvironment containing the neonate once it has been determined that the water age has exceeded the preset expiration time. An expiration alert is generated at step 138 to alert the clinician of the need for cleaning the reservoir 6.

Figure 5A:
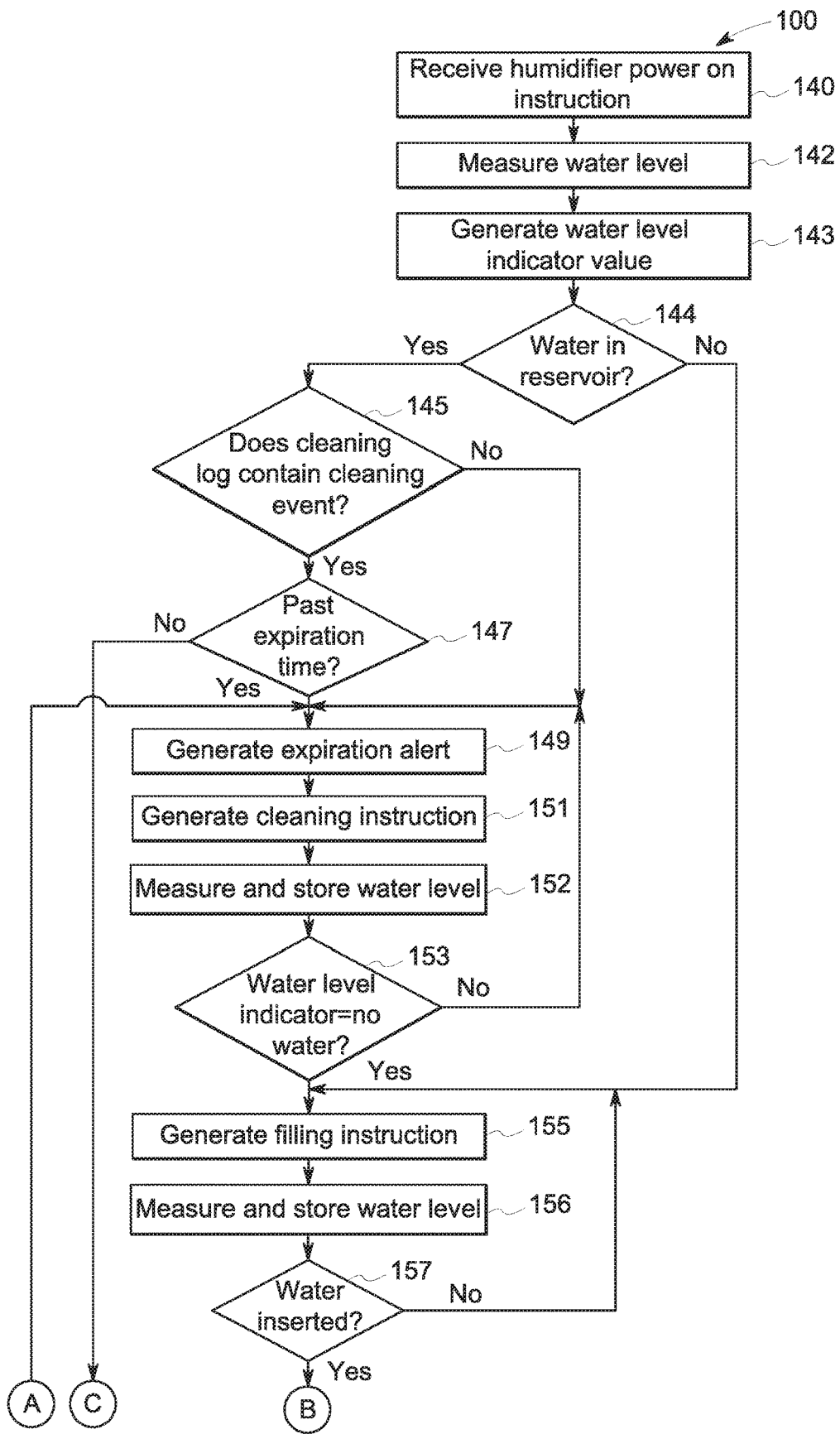
FIGS. 5A and 5B depict another embodiment of a method of controlling an incubator system.
Figure 5B:
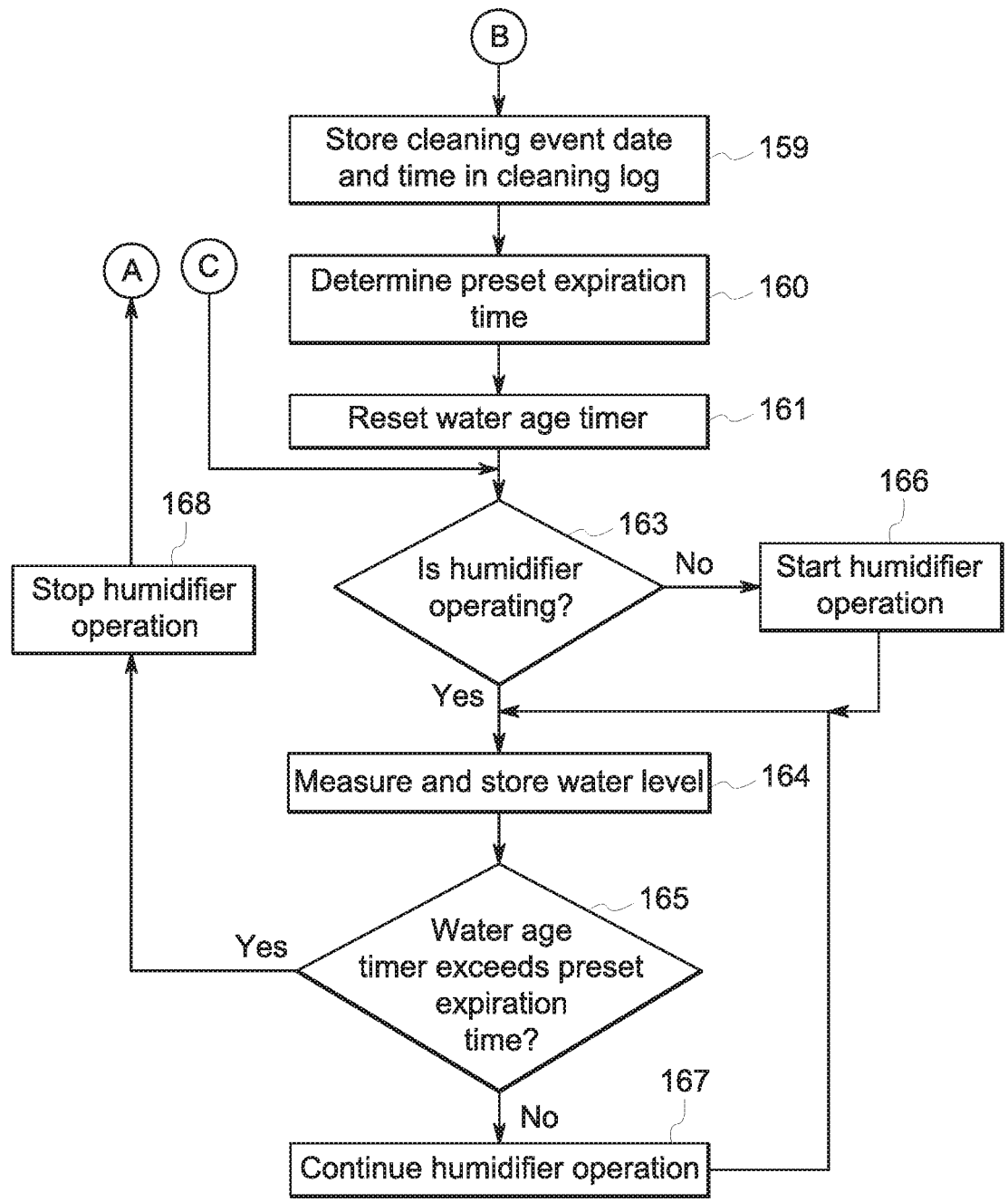

FIGS. 5A and 5B depict another embodiment of a method 100 of controlling an incubator system 1. The input is received at step 140 instructing the humidifier to be powered on, and a water level is determined at step 142 before commencing operation of the humidifier (e.g. before operating the humidifier to disperse any water from the water reservoir 6. For example, the water level may be determined based on the water level indicator value received from the water level sensor 8. Steps are executed to measure a water level and generate a water level indicator value, represented at step 143, and to determine whether the reservoir 6 contains water or is empty, at step 144. If the reservoir 6 is empty, then the method continues to step 155 where a filling instruction is generated. If the reservoir 6 does contain some amount of water, then the system continues to step 145 to determine whether information is available regarding a last cleaning event. For example, the cleaning log for the incubator system 1 may be accessed to determine the date and time of the last store cleaning event.

If cleaning event information is not accessible, then the system assumes that the reservoir 6 is in need of cleaning and an expiration alert is generated alerting a clinician to the need for cleaning. If a cleaning event is stored and accessible in the cleaning log, then steps are executed at step 147 to determine whether the expiration time has passed. If the expiration time has not passed then the system determines that operation of the humidifier is permissible and continues to step 163 to determine whether operation of the humidifier should commence. If the expiration time has already passed, then an expiration alert is generated at step 149, such as via the user interface 39 discussed above. A cleaning instruction is also generated at step 151 via the user interface 39 providing instructions to a clinician for cleaning the reservoir 6, which includes removing the expired water from the reservoir 6.

The water level 33 in the reservoir 6 is measured and/or stored at step 152, such as via a water level indicator value generated based on input from the water level sensor 8. For example, the water level 33 may be periodically stored in the cleaning log for the water reservoir 6 to generate a more detailed record of the usage and operation of the humidifier 4 and water reservoir 6.

The water level indicator value is monitored at step 153 to determine whether the reservoir 6 has been emptied. The expiration alert and cleaning instructions continue to be generated until such time as the expired water has been drained from the reservoir 6. Once the water level indicator value indicates that no water remains in the reservoir 6, a filling instruction is generated at step 155 instructing the clinician to fill the reservoir 6. The water level 33 is again measured and stored at step 155, creating a record of the filling. The water level is measured and stored at step 156, generating and storing a water level indicator value in the cleaning log, and the indicator value is monitored at step 157 to determine whether water has been inserted. For example, the requirements of step 157 may be met when any amount of water is detected in the reservoir 6. Alternatively, the system may require that the water level indicator value indicate that a minimum water level 48 is reached before continuing. A cleaning event date and time are stored in the cleaning log at step 159 and a preset expiration time 160 is then calculated. The water age timer 60, or clock, is reset at step 161 to start counting the water age.

Step 163 is executed to determine whether the humidifier is already running or being operated to control the humidity within the chamber 12. If not, then operation of the humidifier is commenced at step 166. The water level 33 is measured and stored and step 164, which may be stored in the cleaning log to create a record of the water level over time as described above. Step 165 is executed to determine whether the water age timer exceeds the preset expiration time. The humidifier 4 continues to be operated as needed to control humidity within the chamber 12 until the water age timer exceeds the preset expiration time, represented at steps 164-167. Once the preset expiration time is exceeded, the humidifier operation is stopped at step 168. The humidifier is stopped at step 168, discontinuing dispersion of water from the water reservoir 6, and the method continues to step 149 to generate the expiration alert and require cleaning of the reservoir 6 as described above.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. An incubator system for a neonate, the incubator system comprising:
   a humidifier having a water reservoir; and
   an incubator control system configured to:
     detect a cleaning event of the water reservoir;
     determine a water age based on a duration since the cleaning event;
     compare the water age to a preset expiration time;
     determine that the water age exceeds the preset expiration time; and
     generate an expiration alert.

2. The incubator system of claim 1, wherein the incubator control system is further configured to stop disbursement of water from the water reservoir by the humidifier upon determining that the water age exceeds the preset expiration time.

3. The incubator system of claim 1, wherein the incubator control system is further configured to generate an instruction to clean the water reservoir after the expiration alert is generated.

4. The incubator system of claim 1, further comprising:
   a water level sensor that senses a water level in the water reservoir and generates a water level indicator value based thereon;
   wherein the cleaning event detection includes determining that the water level indicator value indicates no water at a base of the water reservoir.

5. The incubator system of claim 4, wherein the incubator control system is further configured to store a date and time of the cleaning event and the water age in a cleaning log.

6. The incubator system of claim 5, wherein the incubator control system is further configured to store the water level indicator value over time in the cleaning log.

7. The incubator system of claim 1, wherein the incubator control system is further configured to detect the cleaning event when the water reservoir is removed from the humidifier and then replaced on the humidifier.

8. The incubator system of claim 7, further comprising:
   a water level sensor that senses a water level in the water reservoir and generates a water level indicator value based thereon;
   wherein the incubator control system is further configured to detect the cleaning event when, after the water reservoir is placed back on the humidifier, the water level indicator value indicates no water at a base of the water reservoir.

9. The incubator system of claim 1, wherein the incubator control system is further configured to detect when a water level in the water reservoir is above a minimum, and then set the water age to zero and start a water age timer.

10. The incubator system of claim 1, wherein the incubator control system is further configured to determine the water age and compares the water age to the preset expiration time prior to starting the humidifier.

11. A method of controlling an incubator system for a neonate, the incubator system having a humidifier that disperses water from a water reservoir, the method comprising:
   generating a water level indicator value with a water level sensor based on a water level in the water reservoir;
   detecting, with a processor, a cleaning event of the water reservoir based on the water level indicator value;
   determining, with the processor, a date and time of the cleaning event;
   determining, with the processor, a preset expiration time based on the date and time of the cleaning event;
   determining, with the processor, that a water age exceeds the preset expiration time; and
   generating an expiration alert.

12. The method of claim 11, further comprising stopping disbursement of water from the water reservoir by the humidifier upon determining that the water age exceeds the preset expiration time.

13. The method of claim 11, further comprising generating, via a user interface, an instruction to clean the water reservoir after the expiration alert is generated.

14. The method of claim 11, further comprising storing, with the processor, the date and time of the cleaning event and the water age in a cleaning log.

15. The method of claim 14, further comprising storing, with the processor, the water level indicator value over time in the cleaning log.

16. The method of claim 11, wherein detecting a cleaning event includes determining, with the processor, that the water level indicator value indicates no water at a base of the water reservoir.

17. The method of claim 11, wherein detecting a cleaning event includes determining, with the processor, that the water reservoir is removed from the humidifier and then replaced on the humidifier.

18. The method of claim 17, wherein detecting a cleaning event includes, after the water reservoir is placed back on the humidifier, determining, with the processor, that the water level indicator value indicates no water at a base of the water reservoir.

19. The method of claim 18, further comprising:
   once the cleaning event is detected, detecting, with the processor, that the water level in the water reservoir is above a minimum water level;
   setting, with the processor, the water age to zero; and
   starting a water age timer, with the processor, to track the water age.

20. The method of claim 19, further comprising determining, with the processor, that the water age is less than the preset expiration time prior to starting the humidifier, and disallowing the humidifier to disperse water from the water reservoir if the water age is not less than the preset expiration time.

* * * * *